United States Patent [19]

Norimatsu et al.

[11] 4,266,519
[45] May 12, 1981

[54] SYSTEM FOR CONTROLLING AN OXYGEN CONCENTRATION IN EXHAUST GASES

[75] Inventors: Hideaki Norimatsu; Koichi Furuta, both of Kariya, Japan

[73] Assignee: Nippondenso Co., Ltd., Kariya, Japan

[21] Appl. No.: 964,962

[22] Filed: Nov. 30, 1978

[30] Foreign Application Priority Data

Feb. 17, 1978 [JP] Japan .................................. 53/17771

[51] Int. Cl.³ .............................................. F02D 35/00
[52] U.S. Cl. ..................................... 123/440; 123/489; 73/23
[58] Field of Search .................... 123/32 EE, 119 EC; 60/276, 285; 73/23

[56] References Cited

U.S. PATENT DOCUMENTS

| | | | |
|---|---|---|---|
| 3,915,135 | 10/1975 | Kushida et al. | 123/32 EE |
| 4,140,085 | 2/1979 | Rabus et al. | 123/32 EE |
| 4,153,023 | 5/1979 | Asano et al. | 123/119 EC |
| 4,156,404 | 5/1979 | Anzai | 123/32 EE |
| 4,156,413 | 5/1979 | Taplin | 123/119 EC |

Primary Examiner—Charles J. Myhre
Assistant Examiner—Andrew M. Dolinar
Attorney, Agent, or Firm—Cushman, Darby & Cushman

[57] ABSTRACT

A system for controlling an oxygen concentration in exhaust gases emitted from a combustion engine. An oxygen sensor which changes a resistance in response to a sensed presence and absence of oxygen in exhaust gases is connected in series with an electric power source and a transistor to produce an output voltage indicative of the sensed presence and absence of oxygen. A comparator compares magnitudes of the sensor output voltage with a predetermined magnitude. In response to an output voltage of the comparator, the transistor controls a biasing current flowing from the electric power source to the sensor so that, when either presence or absence of oxygen is sensed, the sensor output voltage is kept substantially at the predetermined magnitude irrespective of temperature dependent changes in the resistance of the oxygen sensor.

7 Claims, 3 Drawing Figures

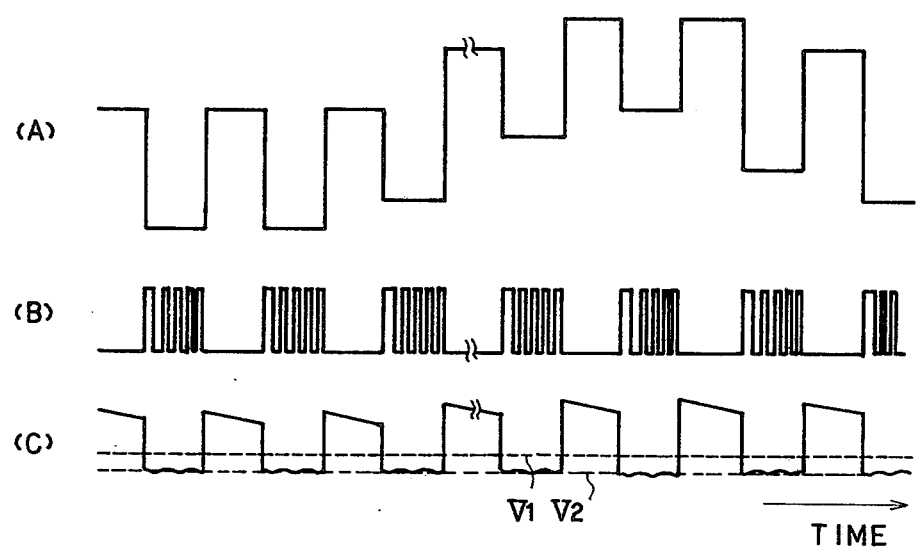

SYSTEM FOR CONTROLLING AN OXYGEN CONCENTRATION IN EXHAUST GASES

BACKGROUND OF THE INVENTION

The present invention relates to a system for controlling an oxygen concentration in exhaust gases emitted from a combustion engine, and more particularly it relates to an improvement in which a biasing current supplied to a resistive type oxygen sensor used to control an oxygen concentration in exhaust gases is varied to keep a sensor output voltage indicative of either presence or absence of oxygen at a predetermined magnitude.

In an engine system in which air-fuel mixtures are supplied to a combustion engine and combustion resultant exhaust gases are emitted from the combustion engine, it is required that the exhaust gases should include less noxious components such as HC, CO and NOx. For this requirement it is suggested that a catalyst effective to reduce the noxious components in the exhaust gases is provided in the exhaust passage. The catalyst presents a high efficiency in reducing the noxious components, when an oxygen concentration in the exhaust gases is kept at a constant value intermediate between a presence and absence of oxygen. Therefore, an air-fuel ratio of the mixture supplied to the combustion engine must be kept substantially at a stoichiometric value (air excess number $\lambda=1$). Alternatively, when the air-fuel ratio of the mixture is below the stoichiometric value, that is, when the mixture is rich in fuel, the exhaust gases must be supplied with air at the upstream of the catalyst. It is most effective to feedback control the air-fuel ratio of mixture supplied to the combustion engine or the amount of air supplied to the exhaust gases in response to the oxygen concentration which may be sensed by an oxygen responsive element.

As the oxygen responsive element, a zirconium dioxide ($ZrO_2$) and a titanium dioxide ($TiO_2$) which exhibit changes in an electromotive force and an resistance respectively in response to the oxygen concentration are known. But such an oxygen responsive element also exhibits changes in the electromotive force or the resistance in response to ambient conditions such as aging and temperature. Therefore, the output changes of the oxygen responsive element resulting from ambient conditions other than the oxygen concentration must be reduced so that the air-fuel ratio of mixture supplied to the combustion engine or the amount of air supplied to the exhaust gases is feedback controlled in response to the output of the oxygen responsive element.

SUMMARY OF THE INVENTION

It is therefore a primary object of the invention to reduce output changes of an oxygen sensor resulting from ambient conditions other than an oxygen concentration.

It is a further object of the invention to feedback control an output signal of an oxygen sensor in response to the output signal of the same.

It is a still further object of the invention to control a biasing current supplied to a resistive type oxygen sensor.

BRIEF DESCRIPTION OF THE DRAWING

In the accompanying drawing:

FIG. 3 is a chart showing resistance changes (A) and signal changes (B) and (C) in the embodiment shown in FIG. 2.

DETAILED DESCRIPTION OF THE PREFERRED EMBODIMENT

Figure 1:
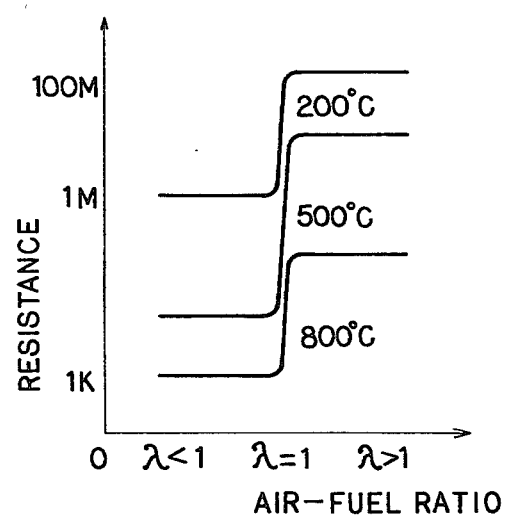
FIG. 1 is a graph showing resistance characteristics of an resistive type oxygen sensor used in the present invention.

The present invention is described hereinunder with reference to an embodiment in which a resistive type oxygen sensor is used to control an air-fuel ratio of mixture supplied to a combustion engine. As shown in FIG. 1, the resistive type oxygen sensor comprising an oxygen responsive element $TiO_2$ exhibits a relatively small and large resistances in response to the absence and presence of oxygen, respectively. Since the absence and presence of oxygen in an exhaust gases result from the combustion of mixtures rich in fuel and in air, respectively, the absence and presence of oxygen represent the small air-fuel ratio (air excess number $\lambda<1$) and the large air-fuel ratio (air excess number $\lambda>1$), respectively. The resistance of the sensor changes stepwisely between the relatively small and large values at a stoichiometric air-fuel ratio (air excess number $\lambda=1$). The resistance of the oxygen sensor also changes in response to the ambient temperature, or the temperature of exhaust gases. For example, the resistance changes between 1 kiloohm and 100 kiloohms at a high temperature 800° C., between 10 kiloohms and 10 megaohms at an intermediate temperature 500° C., and between 1 megaohm and 100 megaohms at a low temperature 200° C.

Figure 2:
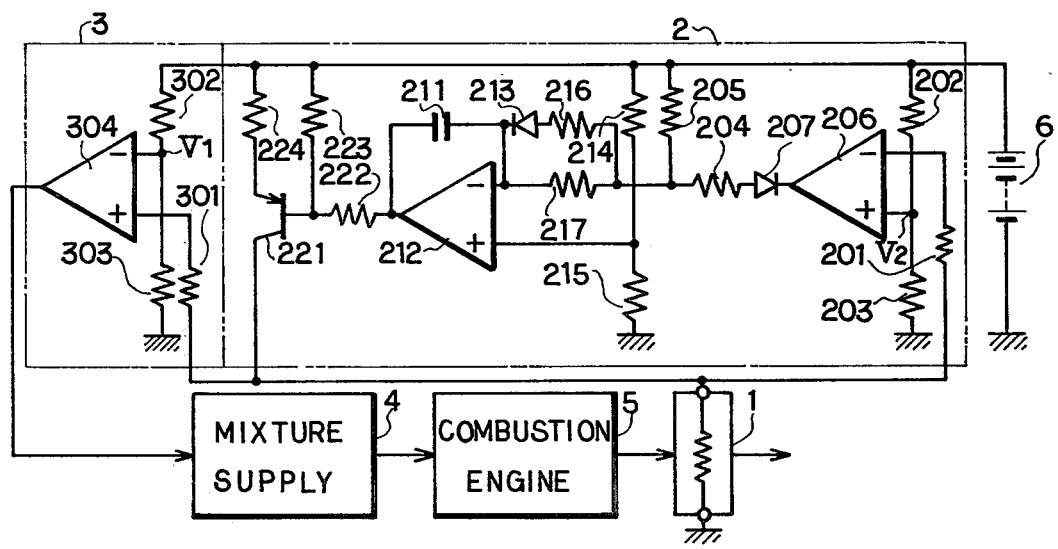
FIG. 2 is an electric wiring diagram showing an embodiment of the present invention.

As shown in FIG. 2, the oxygen sensor 1 is provided in the exhaust passage of an internal combustion engine 5 which is supplied with an air-fuel mixture from a mixture supply device 4 such as a carburetor or the like. The oxygen sensor 1 is grounded at one end and connected to a comparison circuit 3 comprising resistors 301, 302, 303 and a comparator 304. As described later in detail, the oxygen sensor 1 is electrically biased by a biasing circuit 2 and a source of electric power 6 so that the resistance of the sensor 1 is represented by its output voltage.

When the mixture supplied to the engine 5 is rich in fuel, the output voltage of the sensor 1 has a small magnitude in response to the relatively small resistance indicative of the absence of oxygen in the exhaust gases emitted from the engine 1. On the other hand, when the mixture is rich in air, the output voltage has a large magnitude in response to the relatively large resistance indicative of the presence of oxygen. Receiving the output voltage of the sensor 1 through the resistor 301, the comparator 304 compares it with a predetermined magnitude $V_1$ of a reference voltage produced by the resistors 302 and 303. The predetermined magnitude $V_1$ is indicative of the oxygen concentration resulting from the complete combustion of a stoichiometric air-fuel mixture. The comparator 304 produces a comparison resultant output voltage having a constant small magnitude and a constant large magnitude which is indicative of the absence and presence of oxygen, respectively. The mixture supply device 4 decreases and increases the amount of fuel supplied to the engine 5 in response to the constant small and large magnitudes of the output voltage of the comparison circuit 3, respectively. Alternatively, the mixture supply device 4 may increase and decrease the amount of air supplied to the engine in response to the constant small and large magnitudes of the output voltage of the comparison circuit 3, respectively. Controlling thus the air-fuel ratio of mixture supplied from the mixture supply device 4 to the combustion engine 5 in response to the sensed absence and presence of oxygen, the oxygen concentration in the exhaust gases can be kept substantially at a constant value intermediate between the absence and presence of oxygen.

The biasing circuit 2 which reduces the temperature dependent changes in the output voltage of the oxygen sensor 1 comprises resistors 201, 202, 203, 204, 205, 214, 215, 216, 217, 222, 223, 224, a comparator 206, an operational amplifier 212, a transistor 221, diodes 207, 213 and a capacitor 211. The comparator 206 is connected to the oxygen sensor 1 through the resistor 201 and to the junction between the resistors 202 and 203 which produce another reference voltage having a predetermined magnitude $V_2$ smaller than the predetermined magnitude $V_1$. The operational amplifier 212 which constitute an integrator in association with the capacitor 211 is connected to the output of the comparator 206 through the resistors 204, 216, 217 and diodes 207 and 213. The output of the integrator is connected to the base of the transistor 221 the emitter-collector path of which is connected in series with the source of electric power 6, the resistor 224 and the oxygen sensor 1.

In operation, the oxygen sensor 1 is biased by the electric power source 6 through the resistor 224 and the transistor 221 to produce the output voltage in response to its resistance. Provided that the resistance of the sensor 1 is relatively large as shown in (A) of FIG. 3 to indicate the presence of oxygen in the exhaust gases, the magnitude of the sensor output voltage is resultantly large and the comparator 206 produces a low level output voltage as shown in (B) of FIG. 3. The capacitor 211 of the integrator is discharged through the resistor 217 to produce an output voltage which increases gradually. Receiving the gradually increasing voltage from the integrator at the base, the transistor 221 gradually decreases the biasing current supplied to the oxygen sensor 1 so that the sensor output voltage responsively decreases as shown in (C) of FIG. 3. With the magnitude of the sensor output voltage being larger than the predetermined magnitude $V_1$, the comparison circuit 3 produces a high level output signal so that the mixture supply device 4 responsively increases the fuel or decreases the air in the air-fuel mixture supplied to the engine 5.

On the other hand, provided that the resistance of the sensor 1 becomes relatively small as shown in (A) of FIG. 3 to indicate the absence of oxygen in the exhaust gases which is resultant from the increase of fuel or the decrease of air in the air-fuel mixture, the magnitude of the sensor output voltage resultantly becomes smaller than the predetermined magnitude $V_2$. The comparator 206 produces a high level output voltage as shown in (B) of FIG. 3 and the capacitor 211 of the integrator is charged through the diode 213 and the resistor 216. The capacitor 211 responsively produces a gradually decreasing output voltage so that the transistor 221 gradually increases the biasing current supplied to the oxygen sensor 1. The resistance of the resistor 216 is desirably smaller than that of the resistor 217 so that the biasing current is increased faster than decreased. When the magnitude of the sensor output voltage increases above the predetermined magnitude $V_2$ in response to the increase in the biasing current, the comparator 206 produces the low level output voltage as shown in (B) of FIG. 3. The capacitor 211 of the integrator is discharged to produce the gradually increasing output voltage. The transistor 221 gradually decreases the biasing current so that the sensor output voltage is decreased below the predetermined magnitude $V_2$.

As long as the resistance of the oxygen sensor 1 is kept relatively small, the biasing current supplied to the oxygen sensor 1 is increased and decreased alternately so that the magnitude of the sensor output voltage is kept substantially equal to the predetermined magnitude $V_2$ as shown in (C) of FIG. 3. Receiving the sensor output voltage kept at the predetermined magnitude $V_2$ smaller than the predetermined magnitude $V_1$, the comparison circuit 3 produces a low level output voltage so that the mixture supply device 4 responsively decreases the fuel or increases the air in the air-fuel mixture supplied to the engine 5.

The embodiment described hereinabove may be modified so that the magnitude of the sensor output voltage indicative of the presence of oxygen in the exhaust gases is kept at a predetermined constant magnitude.

What we claim is:

1. A system for controlling an oxygen concentration in exhaust gases emitted from a combustion engine comprising:
   means for sensing a presence and absence of oxygen in exhaust gases emitted from a combustion engine to produce an output signal having magnitudes respectively indicative of said presence and absence of oxygen;
   means for comparing said magnitudes of said output signal of said sensing means with a predetermined magnitude indicative of a reference concentration between said presence and absence of oxygen;
   means for controlling said oxygen concentration in said exhaust gases toward said reference concentration in response to an output signal of said comparing means; and
   means for controlling either one of said magnitudes of said output signal of said sensing means toward another predetermined magnitude in response to said output signal of said sensing means;
   wherein said sensing means includes an oxygen responsive titanium dioxide, and wherein said latter controlling means includes:
   comparison means for comparing said magnitudes of said output signal of said sensing means with said another predetermined magnitude;
   integration means for integrating an output signal of said comparison means; and
   biasing means for biasing said sensing means by an electric current in response to an output signal of said integration means.

2. A system according to claim 1, wherein said biasing means includes:
   a source of electric power; and
   a transistor having an emitter-collector path connected in series with said source of electric power and said sensing means and having a base connected to be responsive to the output signal of said integration means.

3. A system for controlling the oxygen concentration in the exhaust gas emitted from a combustion engine comprising:

means including titanium dioxide for exhibiting resistance in response to the presence and absence of oxygen in said exhaust gas;

means for supplying said resistance exhibiting means with an electric current to convert said resistance into a voltage signal indicative of the presence and absence of oxygen;

first means for comparing said voltage signal with a first predetermined value indicative of a desired oxygen concentration;

means for controlling the oxygen concentration toward said desired oxygen concentration in response to an output signal of said first comparing means;

second means for comparing said voltage signal with a second predetermined value different from said first predetermined value; and means for controlling said electric current supplied to said resistance exhibiting means in response to an output signal of said second comparing means to thereby keep said voltage signal indicative of one of the presence and the absence of oxygen at said second predetermined value.

4. An apparatus for controlling the concentration of oxygen in the exhaust of a combustion engine comprising:

means responsive to the presence and absence of oxygen in said exhaust and exhibiting an abrupt change in resistance therebetween for sensing the presence and absence of oxygen in said exhaust;

means responsive to an output of said sensing means for minimizing the variation in the concentration of oxygen from a predetermined oxygen concentration level;

means for providing a variable biasing current to said sensing means to obtain a first voltage in response to said abrupt change from a high resistance to a low resistance, relative to one another, said first voltage being indicative of an oxygen concentration varying from said predetermined oxygen concentration in one direction; and to obtain a second voltage in response to said abrupt change from a low resistance to a high resistance, relative to one another, said second voltage being indicative of an oxygen concentration varying from said predetermined oxygen concentration in the other direction; wherein a predetermined one of said first voltage and said second voltage is maintained at an approximately constant level and is substantially insensitive to the slowly changing resistance of said sensing means over a broad range of resistance values;

means for providing a first reference voltage wherein said first voltage is maintained at an approximately constant level equal to the level of said first reference voltage and said second voltage is greater than said first voltage and decreases slowly as a function of time, and wherein said biasing current varying means comprises:

a first comparator responsive to said reference voltage and the voltage across said sensing means;

an integrator responsive to an output of said comparator; and a current generator responsive to an output of said integrator and connected to said sensing means for providing said biasing current.

5. The apparatus as in claim 4 wherein said current generator comprises a transistor, said transistor having a base thereof connected to the output of said integrator and a collector thereof connected to said sensing means whereby said transistor slowly decreases said biasing current in response to a relatively slowly increasing voltage generated by said integrator when the voltage across said sensing means exceeds said first reference voltage, and quickly increases said biasing current in response to a relatively quickly decreasing voltage generated by said integrator when the voltage across said sensing means is less than said reference voltage, thereby causing said first voltage to vary minutely about the level of said reference voltage in order to maintain said first voltage at an approximately constant level, and causing said second voltage to decrease slowly.

6. The apparatus of claim 5 further comprising means for providing a second reference voltage indicative of said predetermined oxygen concentration level, said second reference voltage being greater than said first reference voltage and less than said second voltage, wherein said variation minimizing means comprises a second comparator responsive to said second reference voltage and the voltage across said sensing means and having the output thereof connected to a mixture supply control device.

7. The apparatus of claim 6 wherein an oxygen responsive portion of said sensing means is titanium dioxide.

* * * * *